United States Patent
Zhang et al.

(10) Patent No.: US 10,000,784 B2
(45) Date of Patent: Jun. 19, 2018

(54) CREATININE BIOSENSOR AND METHOD OF USING THE SAME

(71) Applicant: Siemens Healthcare Diagnostics Inc., Tarrytown, NY (US)

(72) Inventors: Wei Zhang, Needham, MA (US); Jingzhong Zhang, Shrewsbury, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days. days.

(21) Appl. No.: 15/509,067

(22) PCT Filed: Sep. 1, 2015

(86) PCT No.: PCT/US2015/047895
§ 371 (c)(1),
(2) Date: Mar. 6, 2017

(87) PCT Pub. No.: WO2016/040048
PCT Pub. Date: Mar. 17, 2016

(65) Prior Publication Data
US 2017/0247736 A1     Aug. 31, 2017

Related U.S. Application Data

(60) Provisional application No. 62/047,314, filed on Sep. 8, 2014.

(51) Int. Cl.
*C12Q 1/00*     (2006.01)
*B82Y 30/00*     (2011.01)
*G01N 27/26*     (2006.01)

(52) U.S. Cl.
CPC .............. *C12Q 1/002* (2013.01); *B82Y 30/00* (2013.01); *C12Q 1/005* (2013.01); *G01N 27/26* (2013.01)

(58) Field of Classification Search
CPC ..... C12Q 1/002; C12Q 1/005; Y10S 435/817; G01N 27/26; G01N 27/30; G01N 27/301; G01N 27/302; G01N 27/327; G01N 27/333; G01N 27/3335; G01N 27/36; G01N 27/40; G01N 27/403; G01N 27/4035
See application file for complete search history.

(56) References Cited

U.S. PATENT DOCUMENTS 3,649,505 A    3/1972    Strickler et al.
3,776,819 A    12/1973    Williams
(Continued)

FOREIGN PATENT DOCUMENTS

EP     0068025 B1     11/1987

OTHER PUBLICATIONS

G. Guilbault et al., Creatinine-Selective Enzyme Electrodes, Analytica Chimica Acta, 152, pp. 223-228, (1983) (Year: 1983).*
(Continued)

*Primary Examiner* — Maris R Kessel
(74) *Attorney, Agent, or Firm* — Kyle D. Petaja

(57) ABSTRACT

This disclosure relates to creatinine biosensors and the uses thereof. More specifically, this disclosure describes potentiometric creatinine sensors which utilizes one or both of a type of enzyme capable of directly producing ammonium ions ($NH_4^+$) as a consequence of coming into contact with a liquid sample and an internal fill solution with a low free ammonium ion concentration.

6 Claims, 1 Drawing Sheet

(56) References Cited

U.S. PATENT DOCUMENTS

| | | | |
|---|---|---|---|
| 4,476,005 A * | 10/1984 | Tokinaga | ............... C12Q 1/002 134/42 |
| 2009/0045056 A1 | 2/2009 | Berberich et al. | |
| 2010/0025265 A1 | 2/2010 | Hsiung et al. | |
| 2013/0220820 A1 | 8/2013 | Pamidi et al. | |
| 2014/0158536 A1 | 6/2014 | Thompson et al. | |

OTHER PUBLICATIONS

International Search Report and Written Opinion of International Application No. PCT/US2015/047895 dated Dec. 3, 2015.
European Search Report and Written Opinion of European Application No. 15839509.5 dated Sep. 26, 2017.
Guilbault et al., "Improved Urea Electrode", Anal. Chem., vol. 45, No. 2, Jan. 1, 1973 (Jan. 1, 1973), pp. 417-419.
Kim et al., "Correcting errors associated with blood urea measurements employing nonactin-doped ammonium-selective electrodes"; STN CAPLUS, Jan. 1, 1995 (Jan. 1, 1995), p. 1.

* cited by examiner

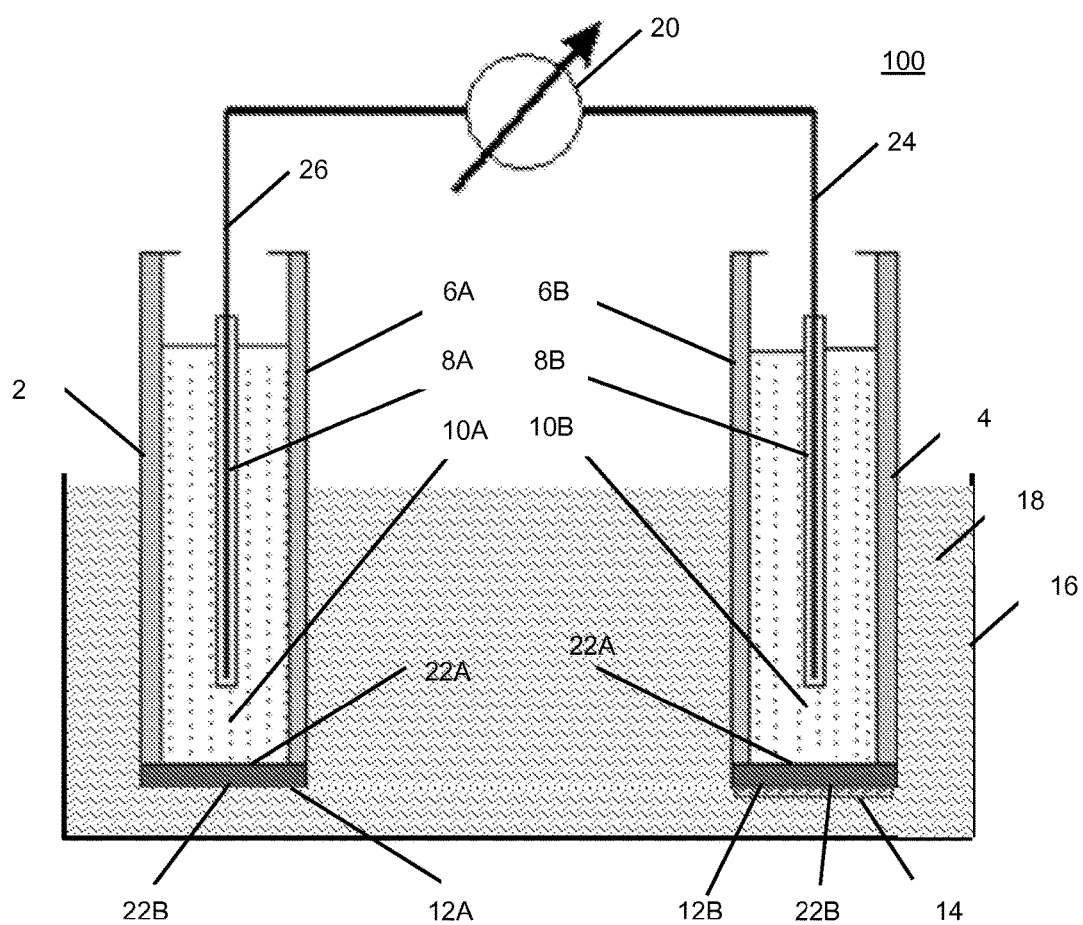

CREATININE BIOSENSOR AND METHOD OF USING THE SAME

The subject application claims benefit under 35 USC § 119(e) of U.S. Provisional Application No. 62/047,314 filed Sep. 8, 2014. The entire contents of the above-referenced patent application are hereby expressly incorporated herein by reference.

BACKGROUND

1. Field of the Disclosure

This disclosure relates to creatinine biosensors and the uses thereof. More specifically, this disclosure describes potentiometric creatinine sensors which utilizes one or both of a type of enzyme capable of directly producing ammonium ions ($NH_4^+$) as a consequence of coming into contact with a liquid sample and an internal fill solution with a low free ammonia ion concentration.

2. Brief Description of the Related Art

The presence of creatinine in a patient's blood may, for example, function as an indicator of the patient's renal health as creatinine is a byproduct of muscle metabolism. As such, creatinine levels in a patient's blood sample may be used to assess kidney health as well as how the effectiveness of medication(s). Standard multi-enzyme amperometric creatinine biosensors produce and then measure an electrical current which flows between the biosensor and the blood sample the biosensor is immersed in. Once measured, the resulting current can be used to determine the concentration of creatinine in the blood sample. The current is measured using an active electrode (also referred to as a working electrode) and an inactive electrode (which may also be referred to as a compensation electrode). The electrical current is a byproduct of an enzymatic cascade reaction which begins when the active electrode is inserted into the blood sample.

In a typical example of a standard amperometric creatinine biosensor, three enzymes are immobilized onto the surface of the active electrode: Creatinine Amidohydrolase, Creatine Amidohydrolase, and Sarcosine Oxidase. When the active electrode is inserted into the blood sample, the following cascade reaction occurs: (1) the enzyme Creatinine Amidohydrolase reacts with Creatinine and $H_2O$ in the sample to produce Creatine; (2) the enzyme Creatine Amidohydrolase reacts with the Creatine to produce Sacrosine and Urea; and (3) the Sarcosine Oxidase enzyme reacts with the Sarcosine as well as $O_2$ and $H_2O$ in the sample to produce Glycine, Formaldehyde and $H_2O_2$—which then results in the creation of an electrical current.

This cascade reaction associated with the active electrode may be expressed as follows:

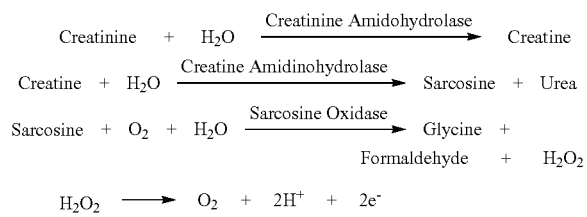

In order to compensate for latent amount of creatine present in the blood sample prior to cascade reaction, the two enzymes are immobilized onto the surface of the inactive electrode: Creatine Amidohydrolase and Sarcosine Oxidase. When the inactive electrode is inserted into the blood sample, the following cascade reaction occurs: (1) the enzyme Creatine Amidohydrolase reacts with the Creatine already present in the blood prior to the insertion of the active electrode to produce Sacrosine and Urea; and (2) the Sarcosine Oxidase enzyme reacts with the Sarcosine as well as $O_2$ and $H_2O$ in the sample to produce Glycine, Formaldehyde and $H_2O_2$— which then results in the creation of an electrical current. By comparing the resulting electrical current recorded by the active and the inactive electrodes, the creatinine concentration in the sample can be determined.

The cascade reaction associated with the inactive electrode may be expresses as follows:

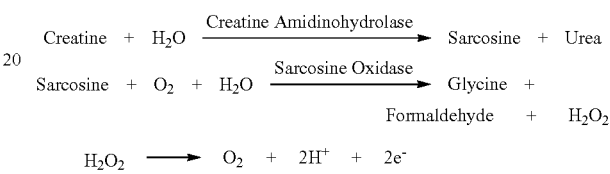

Multi-enzyme amperometric creatinine biosensors have several drawbacks. First, immobilizing three different types of enzymes onto the active electrode and two different types of enzymes onto the inactive electrode complicates manufacturing. Second, during use, the accuracy of the device can be compromised by a failure of just a single enzyme. Such a failure may result manufacturing defects, material defects, contamination, interfering species, etc. . . . . . Third, once produced, the shelf life of these biosensors can be short (for example a matter of weeks).

SUMMARY OF THE INVENTIVE CONCEPT(S)

In one aspect, the inventive concepts disclosed herein are directed to a potentiometric biosensor comprising an active electrode, an inactive electrode, and an internal fill solution. The active electrode comprising an internal fill solution and a first membrane, the first membrane separating the internal fill solution from a liquid sample when the active electrode is inserted into the liquid sample, the first membrane containing a first type of enzyme capable of directly producing ammonium ions ($NH_4^+$) as a consequence of coming into contact with the liquid sample and being devoid of a second type of enzyme. The active electrode comprising the internal fill solution and a second membrane, the second membrane separating the internal fill solution from the liquid sample when the inactive electrode is inserted into the liquid sample, the second membrane being devoid of enzymes capable of directly producing ammonium ions ($NH_4^+$) as a consequence of coming into contact with the liquid sample. The internal fill solution having a total ammonium ion concentration (which includes complexed ammonium and free ammonium) in the range of 1 to 10 mM and a free ammonia ion concentration of three or four orders of magnitude lower than the total ammonium ion concentration.

BRIEF DESCRIPTIONS OF THE DRAWINGS

FIG. 1 illustrates one embodiment of a potentiometric creatinine biosensor.

DETAILED DESCRIPTION OF THE INVENTIVE CONCEPT(S)

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The inventive concepts disclosed herein are generally directed to potentiometric creatinine sensors which utilizes one or both of a type of enzyme capable of directly producing ammonium ions ($NH_4^+$) as a consequence of coming into contact with a liquid sample and an internal fill solution with a low free ammonium ion concentration. Referring to FIG. 1, an exemplary embodiment of such an potentiometric creatinine biosensor 100 includes an inactive electrode 2 and an active electrode 4. The inactive electrode 2 and the active electrode 4 may each include a respective body 6A, 6B, an internal electrode conductor element 8A, 8B, an internal fill solution 10A, 10B (which may also be referred to as an internal fill solution, an internal electrolyte solution, or a reference solution), and an ion sensitive membrane 12A, 12B. The body 6A, 6B for each of inactive electrode 2 and an active electrode 4 may take a variety of shapes and sizes (such as, for example, cylindrical or rectangular) and be constructed out of a glass or any other material known to a person skilled in the art. Each internal electrode conductor element 8A, 8B may be, for example, an electrically conductive wire which extends between a point within the body 6A, 6B of the respective inactive electrode 2 and active electrode 4 to an external measurement device 20 (for example a volt meter, which may be alone or in combination with another computing device). As will be described herein, both the inactive electrode 2 and the active electrode 4 are ammonium ($NH_4^+$) ion-selective electrodes. As should be appreciate by those skilled in the art, FIG. 1 depicts but one illustrative configuration of potentiometric creatinine biosensor 100 and that inactive electrode 2 and active electrode 4 may be arranged differently with respect to one another.

The internal fill solution 10A, 10B may refer to a solution having a fixed, known composition and characteristics contained within each body 6A, 6B. Internal fill solution 10A, 10B includes $NH_4^+$ and one or both of a chelator and a buffer solution. When combined in the proper concentrations, the $NH_4^+$ and a chelator result in an internal fill solution 10A, 10B with a low concentration of free ammonium ions as compared to the total concentration of ammonium ions (which includes complexed ammonium and free ammonium ions). In one example, the internal fill solution maybe comprised of: $NH_4NO_3 + AgNO_3$ + buffer solution—with respective concentrations of, for example, 10 mM of $NH_4NO_3$; 2.46 mM of $AgNO_3$; and 20 mM of the buffer solution. As should be appreciated by one of ordinary skill in the art, the Ag in the above internal fill solution 10A, 10B is but one example of a chelator. Other examples of chelators include Zn and Pt. The presence of a chelator in the internal fill solution 10A, 10B results in the following reaction:

$$2NH_4^+ + Ag^+ \rightleftharpoons Ag(NH_3)_2^+ + H^+ \quad (1)$$

Additionally, when buffer solution has an basic pH level, for example, between 9-11, the basic buffer solution will help the chelator (e.g., Ag, Zn, and Pt) more readily complex with the $NH_4^+$ in the internal fill solution. For example, such a basic buffer solution may result in the formation constant, $K_f$, for equation (1) being $10^7$. The result is an internal fill solution 10A, 10B with a concentration of free ammonium ions of about 0.1 mM. Additionally, the remaining ammonium ions in the internal fill solution 10A, 10B act as a reservoir during the use of the device 100.

According to various embodiments, one or more of, for example: (1) the ratio of $NH_4^+$ and the chelator in the internal fill solution; (2) the type of chelator(s) used; and (3) the pH value of the buffer solution can be adjusted to achieve a low concentration of free ammonium ions in the internal fill solution 10A, 10B. For example, the concentration of free ammonium ions in various embodiments of the internal fill solutions may be 3, 4, 5, 6, 7, or 8 orders of magnitude lower than the total concentration of ammonium ions in the internal fill solution. For example, the internal fill solution may have any of the following concentrations of total ammonium and free ammonium ions, respectively: 1 mM and 1 µM; 1 mM and 100 nM; 10 mM and 10 µM; 10 mM and 1 µM; and 10 mM and 0.1 mM.

It should be further understood that device 100 may function with an internal fill solution 10A, 10B that has a low concentration of free ammonium ions but is devoid of one or both of the chelator or the buffer solution. However, such an internal fill solution 10A, 10B may have a short shelf life. Thus, by including one or both of the chelator or the buffer solution in the internal solution 10A, 10B, stability may be improved and shelf life of the device extended.

The ion sensitive membranes 12A, 12B may be made from, for example, PVC, glass, crystal, or any other type of material know to a person of ordinary skill in the art and have opposing surfaces 22A, 22B. Opposing surfaces 22A, 22B contact the internal fill solution 10A, 10B and sample liquid 18, respectively. The ion sensitive membranes 12A, 12B are integrated into the body 6A, 6B of each respective electrode such that the internal fill solution 10A, 10B is prevented from contacting the liquid sample 18. As an example, ion sensitive membranes 12A, 12B are ammonium ion-specific.

The ion sensitive membrane 12B of the active electrode 4 contains one or more ammonium ion ($NH_4^+$) producing enzymes 14 (hereinafter 'enzyme(s) 4') immobilized onto the surface 22B of the ion sensitive membrane 12B and which produce ammonium ions ($NH_4^+$) upon coming into contact with sample liquid 18. Enzyme 14 may be any type of enzyme capable of reacting with creatinine in the liquid sample 18 in order to directly produce ammonium ions ($NH_4^+$) as a direct consequence of coming into contact with liquid sample 18. For example, two types of enzyme 14 include creatinine iminohydrolase (CIH) and creatinine deimianase (CD). Other types of enzyme 14 may be understood to someone of ordinary skill in the art.

In one embodiment, the ion sensitive membrane 12B of the active electrode 4 comprises a single type of enzyme 14 which produces ammonium ion ($NH_4^+$) upon coming into contact with sample liquid 18 and is devoid of another type of enzyme which directly produces ammonium ion ($NH_4^+$) upon coming into contact with sample liquid 18. In another embodiment, the ion sensitive membrane 12B of the active electrode 4 comprises two or more types of enzyme 14—each of which produces ammonium ion ($NH_4^+$) upon coming into contact with sample liquid 18. The ion sensitive membrane 12A of the inactive electrode 2 does not contain a substantial amount of enzyme 14. In should be understood that, in various embodiments, active electrode 4 and inactive electrode 2 may contain other types of enzymes which do not react with creatinine in the liquid sample 18 in order to directly produce ammonium ions ($NH_4^+$) in the liquid sample 18. Any enzymatic reaction which does not directly product ammonium ions ($NH_4^+$) in the liquid sample 18 can be ignored during the computation of creatinine in the liquid sample 18.

An illustrative use of potentiometric creatinine biosensor 100 will now be described. Upon insertion of the active electrode 4 in liquid sample 18 (sample liquid 18 may be blood or urine) contained in a sample container 16, the immobilized enzyme 14 on the surface 22B of the ion sensitive membrane 12B catalyzes the hydrolysis of creatinine with water ($H_2O$) in the sample to produce, among other compounds, ammonium ions ($NH_4^+$). This reaction may be expressed as follows:

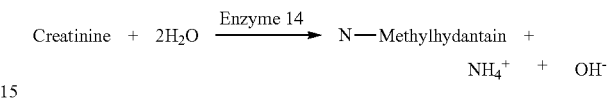

The ammonium ions ($NH_4^+$) created during this reaction are located in an area adjacent to surface 22B of ion sensitive membrane 12B and result in an increase in the electrical potential between opposing surfaces 22A, 22B of the ion sensitive membrane 12B as the number of ammonium ions ($NH_4^+$) in the area of the sample liquid 18 adjacent to the ion sensitive membrane 12B increase as compared to the number of ammonium ions ($NH_4^+$) in the internal fill solution 10B (which is held constant). This electrical potential is picked up by internal electrode 8B and input into measuring instrument 20 as measurement signal 24. This electrical potential may be measured in, for example, mV.

Typically, sample liquid 18 such as blood will contain at least some amount of ammonium ions ($NH_4^+$) prior to the insertion of the active electrode 4 and may interfere with measurement of creatinine in the sample liquid 18. In order to compensate for this interference, inactive electrode 2 is also inserted into the sample liquid 18. Inactive electrode 2 does not contain immobilized enzyme 14 on ion sensitive membrane 12A. As such, the inactive electrode 2 measures electrical potential caused by the different in ammonium ions ($NH_4^+$) concentrations between the sample liquid 18 and the internal fill solution 10 across opposing surfaces 22A, 22B of the ion sensitive membrane 12A. This electrical potential is picked up by internal electrode 8A and input into measuring instrument 20 as compensation signal 26.

In order to identify the change in the electrical potential attributable to only the ammonium ions formed as a result of the reaction of creatinine in the sample liquid 18 with the immobilized enzyme 14, the measuring instrument 20, or a computing device connected to measuring instrument 20, subtracts the value of the compensation signal 26 from the value of measurement signal 24 and outputs the result. Alternatively, a user may use measuring instrument 20 to read compensation signal 26 and measurement signal 24 and manually subtract compensation signal 26 from measurement signal 24. Once computed, the resulting electrical potential value is proportional to the creatinine concentration in the sample liquid 18. Thus, the resulting current can be used to determine the concentration of creatinine in the sample liquid 18.

By utilizing an inactive electrode 2 and the above described internal fill solution 10—with concentration of free ammonium ions in the internal fill solution that is orders of magnitude lower than the total concentration of ammonium ions—illustrative potentiometric creatinine biosensor 100 has a low limit of detection (LLOD) of approximately 2-3 orders of magnitude lower than that of the standard amperometric creatinine biosensor described above. Moreover, the process for immobilizing and fabricating potentiometric creatinine biosensors 100, as described herein, is easier than that of the standard amperometric creatinine biosensor.

What is claimed is:

1. A potentiometric biosensor, comprising:
   an active electrode, wherein the active electrode is an Ammonium ($NH_4^+$) ion-selective electrode and comprises an internal fill solution and a first membrane, the first membrane separating the internal fill solution from a liquid sample when the active electrode is inserted into the liquid sample, the first membrane containing a first type of enzyme capable of directly producing ammonium ions ($NH_4^+$) as a consequence of coming into contact with the liquid sample and being devoid of a second type of enzyme;
   an inactive electrode, wherein the inactive electrode is an Ammonium ($NH_4^+$) ion-selective electrode and comprises the internal fill solution and a second membrane, the second membrane separating the internal fill solution from the liquid sample when the inactive electrode is inserted into the liquid sample, the second membrane being devoid of enzymes that are capable of directly producing ammonium ions ($NH_4^+$) as a consequence of coming into contact with the liquid sample; wherein the first and the second membranes are ammonium ion-specific; and
   the internal fill solution having a total ammonium ion concentration in the range of 1 to 10 mM and a free ammonium ion concentration of three or four orders of magnitude lower than the total ammonium ion concentration, wherein the total ammonium ion concentration includes complexed ammonium ions and free ammonium ions.

2. The potentiometric biosensor of claim 1, wherein the first type of enzyme, when placed in contact with the liquid sample, reacts with creatinine present in the liquid sample to produce ammonium.

3. The potentiometric biosensor of claim 1, wherein the first type of enzyme is one of creatinine iminohydrolase (CIH) or creatinine deimianase (CD).

4. The potentiometric biosensor of claim 1, further comprising a voltmeter electrically coupled to the active electrode and the inactive electrode.

5. The potentiometric biosensor of claim 1, wherein the free ammonium ion concentration is three orders of magnitude lower than the total ammonium ion concentration.

6. The potentiometric biosensor of claim 1, wherein the free ammonium ion concentration is four orders of magnitude lower than the total ammonium ion concentration.

* * * * *